US012642447B2

(12) United States Patent
    Zink et al.

(10) Patent No.: US 12,642,447 B2
(45) Date of Patent: Jun. 2, 2026

(54) MAGNETIC RESONANCE APPARATUS WITH DETACHABLE ARRANGEMENT OF A GUIDE RAIL UNIT

(71) Applicant: Siemens Healthineers AG, Forchheim (DE)

(72) Inventors: Stephan Zink, Nuremberg (DE); Rainer Kurth, Erlangen (DE); Martin Schramm, Eckental (DE); Christian Hetz, Bretzfeld (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 18/953,279

(22) Filed: Nov. 20, 2024

(65) Prior Publication Data

US 2025/0176851 A1     Jun. 5, 2025

(30) Foreign Application Priority Data

Nov. 30, 2023     (EP) ..................................... 23213237

(51) Int. Cl.
    *A61B 5/00*        (2006.01)
    *A61B 5/055*       (2006.01)

(52) U.S. Cl.
    CPC .............. *A61B 5/055* (2013.01); *A61B 5/704* (2013.01)

(58) Field of Classification Search
    CPC ................................. A61B 5/055; A61B 5/704
    See application file for complete search history.

(56) References Cited

U.S. PATENT DOCUMENTS

| | | | |
|---|---|---|---|
| 2006/0197530 A1* | 9/2006 | Damadian | .......... G01R 33/3806 |
| | | | 324/318 |
| 2016/0135896 A1 | 5/2016 | Fink | |
| 2016/0354097 A1* | 12/2016 | Quearry | ............... A61B 17/221 |
| 2018/0110485 A1* | 4/2018 | Tamaoki | .............. A61B 6/0421 |
| 2022/0022829 A1 | 1/2022 | Oakes et al. | |
| 2022/0192603 A1 | 6/2022 | Zink et al. | |
| 2023/0408615 A1* | 12/2023 | Weiss | ............... G01R 33/56509 |

FOREIGN PATENT DOCUMENTS

| | | | | |
|---|---|---|---|---|
| CN | 110722864 A | 1/2020 | | |
| DE | 202022105292 U1 | 10/2022 | | |
| EP | 3682802 A1 * | 7/2020 | ............. | A61B 5/055 |
| EP | 4014855 A1 | 6/2022 | | |
| JP | 2023074336 A * | 5/2023 | | |

OTHER PUBLICATIONS

The JP-2023074336-A machine translation (Year: 2023).*

* cited by examiner

*Primary Examiner* — Alexei Bykhovski
(74) *Attorney, Agent, or Firm* — Banner & Witcoff, Ltd.

(57) ABSTRACT

The disclosure relates to a magnetic resonance apparatus with a scanner unit; a patient accommodation region surrounded at least in part by the scanner unit, the scanner unit having an enclosure at least in part surrounding the patient accommodation region; and a patient positioning apparatus with a movable patient table. The patient table may be configured to be advanceable into the patient accommodation region, the magnetic resonance apparatus having at least two different guide rail units, the at least two different guide rail units having different guide heights for guiding the patient table within the patient accommodation region and the at least two different guide rail units being interchangeably positionable on the enclosure.

18 Claims, 5 Drawing Sheets

MAGNETIC RESONANCE APPARATUS WITH DETACHABLE ARRANGEMENT OF A GUIDE RAIL UNIT

CROSS-REFERENCE TO RELATED APPLICATIONS

The present application claims priority to and the benefit of European patent application no. EP 23213237.3, filed on Nov. 30, 2023, the contents of which are incorporated herein by reference in their entirety.

TECHNICAL FIELD

The present disclosure relates to a magnetic resonance apparatus with a scanner unit, a patient accommodation region surrounded at least in part by the scanner unit, the scanner unit having an enclosure at least in part surrounding the patient accommodation region, and a patient positioning apparatus with a movable patient table, the patient table being configured to be advanceable into the patient accommodation region.

BACKGROUND

Magnetic resonance apparatuses usually have a patient accommodation region in which a patient is placed and/or positioned for an examination, e.g. a magnetic resonance examination. In this case, the patient, e.g. the region of the patient to be examined, is preferably positioned at an isocenter of the magnetic resonance apparatus so as to achieve ideal conditions for acquiring magnetic resonance data. The patient is positioned for this purpose on a patient table of a patient positioning apparatus. For horizontal positioning and/or positioning in the z direction of the magnetic resonance apparatus, the patient table is shifted and/or displaced in the z direction within the patient accommodation region until the region of the patient to be examined is positioned at the isocenter.

In the case of cylindrically configured patient accommodation regions of magnetic resonance apparatuses, the patient table has a single position in the vertical direction within the patient accommodation region. This position in the vertical direction is defined by guide rails which are arranged on an enclosure surrounding the patient accommodation region. This position enables positioning within the patient accommodation region, e.g. in the vertical direction with regard to the isocenter, which is substantially optimal for an average patient. However, this position in the vertical direction represents a positioning compromise for patients who differ significantly in anatomy from the average patient. For babies, small children, or severely obese patients, positioning at the isocenter in the vertical direction is difficult or impossible since the position of the patient table is not variable and/or adjustable in the vertical direction. This means that the patient table always adopts the same position in the vertical direction irrespective of patient anatomy and/or the type of magnetic resonance examination.

To adapt to the position of the patient in the vertical direction, it has hitherto been necessary to bring the patient into a desired position using additional positioning aids, for example positioning pads. Such positioning is time-consuming for a medical operator, however, and only upward adaptation is possible. That is, it is not possible to lower the patient table within the patient accommodation region using such procedures.

SUMMARY

The object of the present disclosure is directed to enabling flexible positioning of a patient table within a patient accommodation region. The object is achieved by the features of the various embodiments as further discussed herein, including in the claims.

The disclosure is directed to a magnetic resonance apparatus with a scanner unit, a patient accommodation region surrounded at least in part by the scanner unit, the scanner unit having an enclosure at least in part surrounding the patient accommodation region, and a patient positioning apparatus with a movable patient table, the patient table being configured to be advanceable into the patient accommodation region. According to the disclosure, the magnetic resonance apparatus has at least two different guide rail units, the at least two different guide rail units having different guide heights for guiding the patient table within the patient accommodation region and the at least two different guide rail units being interchangeably positionable on the enclosure.

The magnetic resonance apparatus may e.g. comprise a medical and/or diagnostic magnetic resonance apparatus that is designed and/or configured to acquire medical and/or diagnostic image data, e.g. medical and/or diagnostic magnetic resonance image data, from a patient. The magnetic resonance apparatus to this end comprises the scanner unit. The scanner unit of the magnetic resonance apparatus mat e.g. comprise a magnet unit for acquiring the medical and/or diagnostic image data. The scanner unit, e.g. the magnet unit, may e.g. comprise a main magnet, a gradient coil unit and a radio-frequency antenna unit. The radio-frequency antenna unit is fixedly arranged within the scanner unit and designed and/or configured to emit an excitation pulse.

Furthermore, the magnetic resonance apparatus has at least one local radio-frequency coil which is configured to receive a magnetic resonance signal. To this end, the local radio-frequency coil is arranged and/or applied around the region of the patient to be examined. The individual local radio-frequency coils may e.g. be designed and/or configured specifically for a patient examination region, such as for example a head radio-frequency coil or a knee radio-frequency coil etc.

The main magnet is configured to generate a homogeneous main magnetic field with a defined magnetic field strength, such as for example with a magnetic field strength of 3 T or 1.5 T etc. The main magnet is e.g. configured to generate a strong and constant main magnetic field. The homogeneous main magnetic field is e.g. arranged and/or to be found within the patient accommodation region of the magnetic resonance apparatus. The gradient coil unit is configured to generate magnetic field gradients that are used for spatial encoding during imaging.

The patient accommodation region is designed and/or configured to accommodate the patient, e.g. the region to be examined of the patient, for a medical magnetic resonance examination. The patient accommodation region may e.g. comprise the region which is available to the patient during a magnetic resonance examination. To this end, the patient accommodation region is for example of cylindrical configuration or cylindrically surrounded by the scanner unit, e.g. the magnet unit, of the magnetic resonance apparatus. The scanner unit, e.g. the magnet unit, here may comprise an enclosure at least in part surrounding the patient accommodation region. The enclosure e.g. surrounds the patient accommodation region cylindrically. The enclosure may here be configured in one piece with the radio-frequency antenna unit of the magnet unit and comprise a side of the radio-frequency antenna unit facing the patient accommodation region.

A field of view (FOV) and/or an isocenter of the magnetic resonance apparatus is preferably arranged within the patient accommodation region. The FOV e.g. comprises an acquisition region of the magnetic resonance apparatus, within which prevail the conditions for acquiring medical image data, e.g. magnetic resonance image data, within the patient accommodation region, such as for example a homogeneous main magnetic field. The isocenter of the magnetic resonance apparatus may e.g. comprise the region and/or point within the magnetic resonance apparatus that has the optimum or ideal conditions for acquiring medical image data. The isocenter may e.g. comprise the most homogeneous region of the magnetic field within the magnetic resonance apparatus.

The magnetic resonance apparatus has the patient positioning apparatus for positioning the patient, e.g. the region of the patient to be examined, within the patient accommodation region. The patient positioning apparatus is configured for positioning the patient. The patient positioning apparatus may e.g. have a movable patient table which is configured to be movable e.g. within the patient accommodation region of the magnetic resonance apparatus. The patient table may e.g. be configured to be movable within the patient accommodation region in the longitudinal direction of the patient accommodation region. In addition, the patient table is also configured to be movable in the vertical direction, the patient table being adjusted in the vertical direction to the height of a guide rail arranged within the patient accommodation region prior to being advanced into the patient accommodation region.

To adjust a position of the patient table, the patient positioning apparatus also has an adjusting unit. The adjusting unit has a vertical adjusting unit for adjusting a vertical position and/or height of the patient table. In addition, the adjusting unit has a horizontal adjusting unit for adjusting a horizontal position of the patient table, e.g. in the longitudinal direction of the patient accommodation region, within the patient accommodation region.

For a magnetic resonance examination, the patient is initially positioned on the patient table of the patient positioning apparatus. Then the patient table is adjusted together with the patient to a height and/or vertical position of the guide rail. The patient table together with the patient is then advanced into the patient accommodation region, e.g. in the longitudinal direction of the patient accommodation region, until the region of the patient to be examined is positioned within the isocenter.

Furthermore, the magnetic resonance apparatus has at least two different guide rail units. The guide rail units are configured for guiding and/or positioning, e.g. movably guiding and/or positioning, the patient table within the patient accommodation region. The at least two different guide rail units differ in terms of a guide height and/or vertical position for the patient table within the patient accommodation region. The at least two different guide rail units are e.g. of like construction with regard to securing and/or arrangement, e.g. detachable securing and/or arrangement, on the enclosure.

Each of the guide rail units has at least one guide rail for guiding the patient table. In addition, the guide rail units may also have two or more guide rails, the individual rails having different vertical positions. The guide rail units may e.g. be arranged on the enclosure within the patient accommodation region in such a way that the guide rail faces the patient accommodation region. Securing elements arranged on the guide rail unit for positioning and/or arrangement on, e.g. detachable securing to, the enclosure are, on the other hand, arranged on a side of the guide rail unit facing the enclosure. The guide rail units may here in each case have at least two guide rails which, on positioning the guide rail unit on the enclosure, are positioned and/or arranged on different sides, e.g. on opposing sides, of the enclosure. Alternatively, the guide rail units may also be arranged interchangeably on just one side of the enclosure, such that a guide rail unit on both sides for guiding the patient table, the two guide rail units having the same guide height for guiding the patient table within the patient accommodation region.

The interchangeable positioning and/or interchangeable arrangement of the guide rail units on the enclosure here means that the corresponding guide rail unit is positioned and/or arranged on the enclosure depending on the desired vertical position of the patient table. Guide rail units that are already arranged within the enclosure but are not in the desired vertical position for the patient table are demounted in advance from the enclosure and removed from the patient accommodation region. The guide rail units may e.g. be arranged and/or secured removably on the enclosure. The guide units may here be arranged and secured on the enclosure within the patient accommodation region depending on the use situation, e.g. on the space requirements during a magnetic resonance examination. The space requirements during a magnetic resonance examination may in this case be dependent on the size of the patient and/or the type of examination.

In addition, it is also conceivable for no guide rail unit to be positioned on the enclosure within the patient accommodation region when a self-supporting patient table is being used, so as to have all the more space for introducing the patient table together with the patient.

The disclosure has the advantage that a position of the patient table may be adapted to space requirements in the vertical direction during a magnetic resonance examination. For instance, in the case of elevated space requirements for a magnetic resonance examination, guide rail units having a lower guide height than the standard patient table guide height may be arranged on the enclosure. Alternatively, when carrying out magnetic resonance examinations on toddlers and/or babies, for example, guide rail units having a higher guide height than the standard patient table guide height may be arranged on the enclosure. This also enables optimal positioning of the region to be examined of the patient to be examined at the isocenter of the magnetic resonance apparatus in terms of height and/or vertical orientation. It is consequently also possible to achieve high quality of the acquired image data.

In addition, different patient positioning apparatuses having different guide characteristics within the patient accommodation region may also be used by arranging the corresponding guide rail unit for magnetic resonance examinations on the same magnetic resonance apparatus. For instance, patient tables with different widths may in this case also be used for magnetic resonance examinations.

An additional advantage of the disclosure is that removing the guide rail unit enables simple and rapid cleaning of the patient accommodation region.

In one advantageous development of the magnetic resonance apparatus according to the disclosure, provision may be made for the enclosure to have at least one securing element for detachable arrangement of one of the guide rail units, the guide rail units in each case having a securing element corresponding to the securing element of the enclosure. The corresponding securing elements may e.g. be configured such that, on connection of the corresponding securing elements, the respective guide rail unit is secured and/or arranged, e.g. detachably secured and/or arranged, on to/the enclosure. The at least one securing element of the guide rail unit may in this case have a type of rail, for example a T-shaped rail or a dovetail-shaped rail, which matches a corresponding groove in the enclosure for securing and/or arranging the guide rail unit. Alternatively, the at least one securing element may have a securing pin, for example a mushroom-headed pin, which matches a corresponding hole and/or opening in the enclosure for securing and/or arranging the guide rail unit. In addition, the at least one securing element may also comprise a quick clamping mechanism.

This configuration of the disclosure enables simple and rapid securing and/or arrangement of the guide rail unit on the enclosure. For instance, different guide rail units, which e.g. have different guide heights for the patient table within the patient accommodation region, may be simply and rapidly exchanged for a magnetic resonance examination.

In one advantageous development of the magnetic resonance apparatus according to the disclosure, provision may be made for the enclosure to have at least two securing elements, which are arranged on the enclosure on opposing sides of the patient accommodation region surrounded by the enclosure. In this case, at least one first securing element may be e.g. arranged on a first side of the enclosure and at least one second securing element is arranged on a second side of the enclosure, e.g. on a side of the enclosure opposite the first side of the enclosure. The enclosure may in this case also have more than one first securing element and also more than one second securing element. The at least two securing elements are preferably of like construction. The at least two securing elements may here be configured for arrangement of a single guide rail unit, which may thus be secured on both sides, e.g. the opposing sides, within the patient accommodation region. Alternatively, two guide rail units may also be arranged, e.g. detachably and/or interchangeably arranged, on the enclosure on opposing sides by way of the at least two securing elements. The two opposing sides of the enclosure here comprise a left-hand side and a right-hand side of the enclosure for bilaterally guiding the patient table within the patient accommodation region.

In one advantageous development of the magnetic resonance apparatus according to the disclosure, provision may be made for the at least one securing element of the enclosure to have a positive-locking element. The guide rail units may e.g. in each case have at least one securing element configured as a positive-locking element and configured to be compatible with the positive-locking element of the enclosure. This advantageously enables simple, reliable arrangement and/or securing of the guide rail units.

In one advantageous development of the magnetic resonance apparatus according to the disclosure, provision may be made for the positive-locking element to comprise a groove extending in the longitudinal extent of the patient accommodation region. The groove may here be of T-shaped or indeed dovetail-shaped configuration and/or adopt further forms and/or cross-sections which appear appropriate to a person skilled in the art. The longitudinal extent of the patient accommodation region is here parallel to the direction of advance of the patient table into the patient accommodation region. In addition, the longitudinal extent of the patient accommodation region is parallel to the z direction of the magnetic resonance apparatus. Advantageously, the enclosure has two positive-locking elements configured as grooves which are arranged on opposing, mutually facing sides of the enclosure surrounding the patient accommodation region. This enables stable and reliable securing of the at least one guide rail unit along the entire enclosure of the patient accommodation region. For instance, advantageous support and/or weight distribution over the entire length of the at least one securing element, e.g. of the groove, may be achieved in this way. A further advantage is that the different guide rail units can be changed on the enclosure simply and without using tools.

In one advantageous development of the magnetic resonance apparatus according to the disclosure, provision may be made for the enclosure to comprise at least two securing elements which are configured to secure a guide rail unit. The at least two securing elements may e.g. be arranged on the enclosure one after the other in the longitudinal direction of the patient accommodation region. In addition, the enclosure may also have more than two securing elements for securing and/or arranging a guide rail unit. This configuration of the disclosure has the advantage of achieving stable and reliable arrangement and/or securing, e.g. detachable and/or interchangeable arrangement, of the guide rail unit on the enclosure.

In one advantageous development of the magnetic resonance apparatus according to the disclosure, provision may be made for the scanner unit to comprise a radio-frequency antenna unit, the at least two securing elements in each case being arranged on the enclosure outside an overlap region of the enclosure with the radio-frequency antenna unit. The radio-frequency antenna unit is integrated fixedly within the scanner unit, e.g. the magnet unit. The radio-frequency antenna unit may e.g. be arranged within the scanner unit, e.g. the magnet unit, between the gradient coil unit and the enclosure. The overlap region of the radio-frequency antenna unit with the enclosure surrounding the patient accommodation region here extends in the longitudinal direction of the patient accommodation region and/or in the z direction of the scanner unit, e.g. of the magnet unit. In this case, the overlap region comprises a region in which the radio-frequency antenna unit and the enclosure have the same z coordinate. Arrangement of the at least two securing elements outside the overlap region here encompasses arrangement of the at least two securing elements in a region in which the radio-frequency antenna unit exhibits no extent in the z direction. This configuration of the disclosure has the advantage that undesired impairment of the radio-frequency antenna unit and/or of a magnetic resonance examination can be prevented.

In one advantageous development of the magnetic resonance apparatus according to the disclosure, provision may be made for the at least two securing elements in each case to comprise a hole and/or an opening and/or a peg. The hole and/or opening may e.g. be arranged on a side of the enclosure facing the patient accommodation region. The hole and/or opening is configured to receive a securing element of the guide rail units. The hole and/or opening may additionally comprise a cavity, which is at least in part concealed from a housing side facing the patient accommodation region, for example for receiving a mushroom-headed securing element of the guide rail units. The peg may in this case be of pin-shaped and/or cylindrical configuration. For the purpose of arranging and/or securing the guide rail units, the peg may e.g. be arranged on a side of the enclosure facing the patient accommodation region. In addition, for the purpose of arranging and/or securing the guide rail units, the peg may be arranged removably on the enclosure. This configuration of the disclosure has the advantage of enabling simple arrangement and/or securing of a guide rail unit on the enclosure. For example, rapid, time-saving securing and/or arrangement of a guide rail unit on the enclosure may additionally be achieved.

In one advantageous development of the magnetic reso-nance apparatus according to the disclosure, provision may be made for the different guide rail units in each case to have an encoding, the encoding comprising information relating to the guide height of the respective guide rail unit. The different guide rail units in this case may e.g. have different encoding.

The encoding may e.g. comprise a mechanical encoding and/or an electro-optical encoding. The mechanical encod-ing may for example comprise a plug-in connector and/or a pressure switch and/or further mechanical encoding between the guide rail units and the enclosure which appear appro-priate to a person skilled in the art. A pressure switch of this type may comprise a plurality of pressure points, a different combination of the plurality of pressure points being acti-vatable depending on the type of guide rail unit. In this case, the guide rail unit has a corresponding encoded plug, for example, which may be inserted into a corresponding sensor socket which is arranged, for example, on the enclosure. When arranging and/or securing the guide rail unit on the enclosure, the corresponding mechanical encoding is pref-erably also activated and/or transmitted to the enclosure.

Alternatively or in addition, the encoding may comprise an electro-optical encoding, for example a universal product code and/or a barcode and/or a two-dimensional barcode. In addition, the electro-optical encoding may also comprise an RFID code and/or a reflector and/or further electro-optical encoding which appear appropriate to a person skilled in the art. In the case of different guide rail units, the encoding may e.g. be arranged at the same position on the guide rail unit, so as to enable simple, rapid detection of the encoding.

This configuration of the disclosure enables simple and rapid detection of the guide rail unit arranged on the enclo-sure. For instance, this configuration of the disclosure enables automatic and/or automated detection of the guide rail unit arranged on the enclosure. In this way, an exact height and/or vertical position to which the patient table needs to be raised may also be communicated to a patient table control unit configured to control movement of the patient table before said table can be advanced into the patient accommodation region.

In one advantageous development of the magnetic reso-nance apparatus according to the disclosure, provision may be made for the magnetic resonance apparatus to have at least one detection element for detecting the encoding of one of the guide rail units. If the encoding of the guide rail units comprises a mechanical encoding, the detection element may e.g. comprise a mechanical detection element for detecting the mechanical encoding, such as for example a plug with a defined plug pattern etc. If the encoding of the guide rail units comprises an electro-optical encoding, the detection element may e.g. comprise an electro-optical sen-sor unit and/or reader unit. In this case, the detection element for detecting an electro-optical encoding may be configured for noncontact detection of the electro-optical encoding on the guide rail unit. This enables simple and automatic and/or automated detection of the guide rail unit arranged on the enclosure. In this way, an exact height and/or vertical position to which the patient table needs to be raised may also be communicated to a patient table control unit con-figured to control movement of the patient table before said table can be advanced into the patient accommodation region.

In one advantageous development of the magnetic reso-nance apparatus according to the disclosure, provision may be made for the at least one detection element to be encompassed by the patient positioning apparatus, e.g. the patient table and/or by the enclosure surrounding the patient accommodation region. This provides rapid, direct detection of the guide rail unit arranged on the enclosure. If the patient positioning apparatus, e.g. the patient table, has the at least one detection element, the acquired data may be transmitted directly to a patient table control unit of the patient posi-tioning apparatus. This advantageously enables rapid, direct adjustment of a height and/or vertical position of the patient table.

In one advantageous development of the magnetic reso-nance apparatus according to the disclosure, provision may be made for the magnetic resonance apparatus to have a computing unit, the computing unit using the encoding detected by the at least one detection element to provide a vertical position, which is to be established, of the patient table.

The computing unit is here may e.g. be encompassed by the patient table control unit of the patient positioning apparatus. In this case, the computing unit comprises at least one computing module and/or processor and is configured to execute computer-readable instructions. For instance, the computing unit may comprises a memory unit, computer-readable information being stored in the memory unit, and the computing unit may be configured to load the computer-readable information from the memory unit and execute the computer-readable information. In this way, the computing unit according to the disclosure is configured to use the encoding detected by the at least one detection element to provide a vertical position of the patient table that is to be established. The components of the computing unit may predominantly take the form of software components. In principle, however, these components may also in part, e.g. when rapid calculations are involved, be embodied in the form of software-assisted hardware components, for example FPGAs or the like. Likewise, the necessary inter-faces, for example if it is only a matter of receiving data from other software components, may take the form of software interfaces. They may, however, also take the form of hardware interfaces which are driven by suitable soft-ware. It is, of course, also conceivable for a plurality of the stated components to be combined and embodied in the form of an individual software component or software-assisted hardware component.

The encoding of the guide rail unit detected by the at least one detection element, e.g. the position information of the guide rail unit associated with and/or connected to the detected encoding, is here transmitted to the computing unit, for example by a data transfer unit. Data transmission by the data transmission unit may here be wired or indeed proceed wirelessly and/or without a cable connection. With the assistance of the encoding, e.g. with the assistance of the guide rail unit position information associated with and/or connected to the detected encoding, the computing unit may ascertain a height and/or vertical position of the guide rail of the guide rail unit and ascertain therefrom and provide the position, e.g. the vertical position, of the patient table. The position of the patient table is provided by the computing unit of the patient table control unit to an adjusting unit, e.g. a vertical adjusting unit, of the patient positioning apparatus. This configuration of the disclosure has the advantage of providing direct, rapid adjustment of a height and/or vertical position of the patient table.

In one advantageous development of the magnetic resonance apparatus according to the disclosure, provision may be made for the magnetic resonance apparatus to have at least one auxiliary unit which is integrated at least in part into one of the guide rail units. An auxiliary unit of this type may for example comprise a lighting unit with at least one lighting element and/or light-emitting element for illuminating the patient accommodation region. In this case, the guide rail unit may e.g. have an optical interface and/or an electronic interface for transmitting light signals and/or control signals for controlling the lighting unit integrated within the guide rail unit. Alternatively or in addition, the auxiliary unit may comprise a ventilation opening for supplying air during the magnetic resonance examination. The guide rail unit in this case may e.g. have a ventilation duct and a ventilation interface, the ventilation interface being coupled to a ventilation duct of a ventilation unit encompassed by the magnet unit. Alternatively or in addition, the auxiliary unit may comprise at least one communication element of a patient communication unit. A communication element of this type may, for example, comprise a patient microphone and/or a patient loudspeaker. The guide rail unit may e.g. have a communication interface for this purpose. Alternatively or in addition, further auxiliary units which appear appropriate to a person skilled in the art may be integrated into the at least one guide rail unit.

This configuration of the disclosure enables advantageous and space-saving integration of further units within the patient accommodation region. Further units, which are needed during a magnetic resonance examination, for example for patient safety and/or wellbeing, may in this way be arranged in space-saving manner.

BRIEF DESCRIPTION OF THE DRAWINGS

Further advantages, features and details of the disclosure are revealed by the exemplary embodiments described below with reference to the drawings.

In the figures.

DETAILED DESCRIPTION OF THE DISCLOSURE

Figure 1:
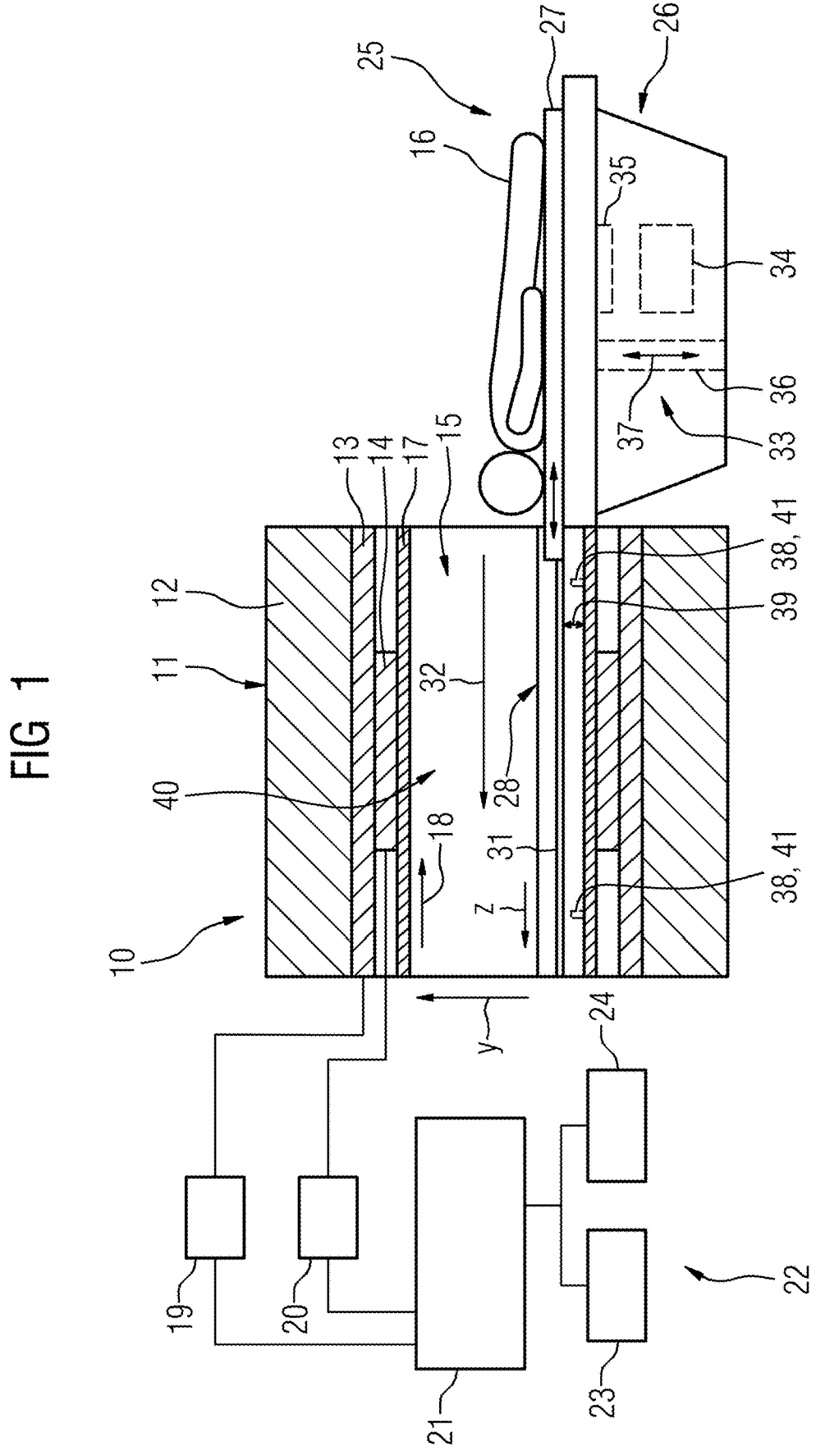
FIG. 1 illustrates a schematic representation of an example magnetic resonance apparatus with a removable guide rail unit on an enclosure, in accordance with one or more embodiments of the disclosure.

FIG. 1 illustrates a schematic representation of an example magnetic resonance apparatus with a removable guide rail unit on an enclosure, in accordance with one or more embodiments of the disclosure. FIG. 1 shows a magnetic resonance apparatus 10 in a schematic manner. The magnetic resonance apparatus 10 comprises a scanner unit (Also referred to herein as a scammer) formed by a magnet unit 11 with a main magnet 12, a gradient coil unit 13 and a radio-frequency (RF) antenna unit 14 (also referred to herein as RF circuitry). The magnetic resonance apparatus 10 additionally comprises a patient accommodation region 15 for accommodating a patient 16 undergoing a magnetic resonance examination. In the present exemplary embodiment, the patient accommodation region 15 is of cylindrical construction and is cylindrically surrounded in a circumferential direction by the magnet unit 11. In principle, however, the patient accommodation region 15 may be formed in any suitable manner, which may differs therefrom for instance. The scanner unit, e.g. the magnet unit 11, additionally has an enclosure 17 surrounding the patient accommodation region 15, the enclosure 17 cylindrically surrounding the patient accommodation region 15. The patient accommodation region 15 here comprises that region which is surrounded by the enclosure 17.

The main magnet 12 of the magnet unit 11 is configured to generate a strong and constant main magnetic field 18. The main magnet 12 may for example take the form of a superconductive main magnet 12 or indeed of a permanent magnet. The gradient coil unit 13 of the magnet unit 11 is configured to generate magnetic field gradients that are used for spatial encoding during imaging. The gradient coil unit 13 is controlled by way of a gradient control unit 19 of the magnetic resonance apparatus 10. The magnet unit 14 of the magnet unit 11 is configured to excite polarization which is established in the main magnetic field 18 generated by the main magnet 12. The radio-frequency antenna unit 14 is controlled by a radio-frequency antenna control unit 20 of the magnetic resonance apparatus 10 and irradiates radio-frequency magnetic resonance sequences into the accommodation region 15 of the magnetic resonance apparatus 10.

The magnetic resonance apparatus 10 has a system control unit 21 for controlling the main magnet 12 and the gradient control unit 19 and for controlling the radio-frequency antenna control unit 20. The system control unit 21 centrally controls the magnetic resonance apparatus 10, such as for example the performance of a predetermined imaging gradient echo sequence. In addition, the system control unit 21 comprises an evaluation unit, not shown in greater detail, for evaluating medical image data which is acquired during the magnetic resonance examination.

The magnetic resonance apparatus 10 furthermore comprises a user interface 22, which is connected to the system control unit 21. Control information, such as for example imaging parameters and reconstructed magnetic resonance images can be displayed on a display unit 23, for example on at least one monitor, of the user interface 22 for a medical operator. The user interface 22 furthermore has an input unit 23, by way of which information and/or parameters may be input by the medical operator during a measurement procedure.

The depicted magnetic resonance apparatus 10 may of course comprise further components which magnetic resonance devices 10 usually have. A general mode of operation of a magnetic resonance device 10 is additionally known to a person skilled in the art and therefore no detailed description of the further components is provided.

The magnetic resonance apparatus 10 has a patient positioning apparatus 25 for positioning the patient 16, e.g. a region of the patient 16 to be examined, within the patient accommodation region 15. The patient positioning apparatus 25 has a base unit 26 and a patient table 27 movable relative to the base unit 26. The patient table 27 is configured to position the object and/or the patient 16, e.g. the region of the patient 16 to be examined, movably within the patient accommodation region 15. As an example, the patient table 27 may be mounted movably in the direction of a longitudinal extent of the patient accommodation region 15 and/or in the z direction. At least one guide rail unit 28 (also referred to herein as a guide rail or guide rail assembly) of the magnetic resonance apparatus 10 is arranged within the patient accommodation region 15. In the present exemplary embodiment, the magnetic resonance apparatus 10 has two guide rail units 28 that are arranged on the enclosure 17 on opposing sides 29, 30 of the patient accommodation region 15. The two guide rail units 28 in each case have at least one guide rail 31, on which the patient table 27 is guided for movement within the patient accommodation region 15 in the longitudinal direction 32 of the patient accommodation region 15.

Figure 2:
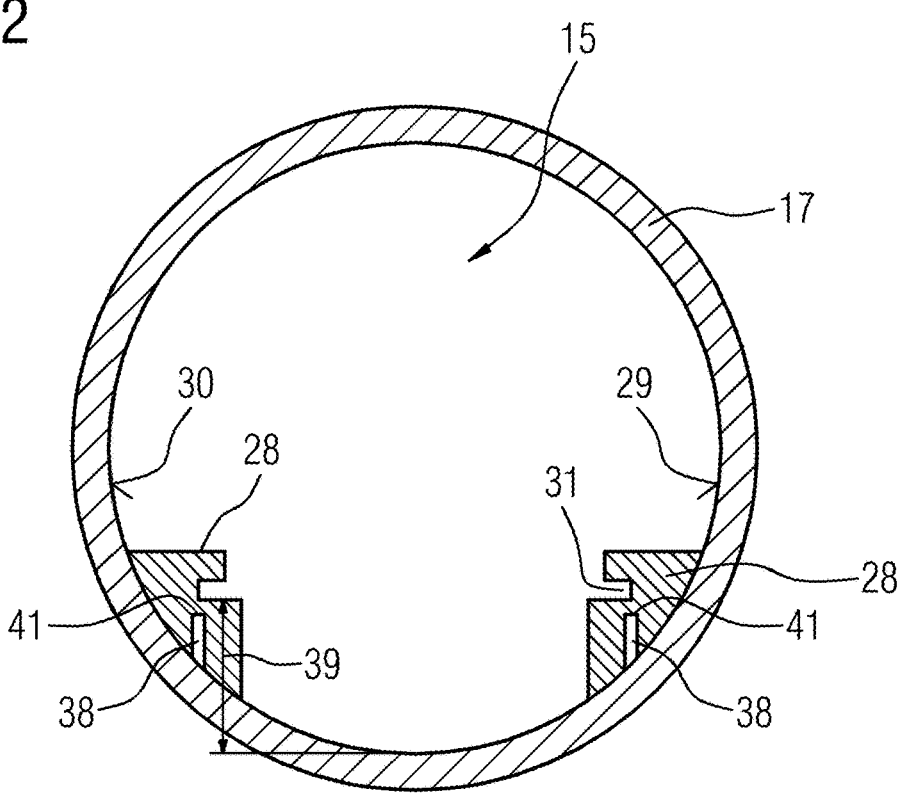
FIG. 2 illustrates an example sectional representation of the guide rail unit with the enclosure, in accordance with one or more embodiments of the disclosure.

The magnetic resonance apparatus 10 additionally has further guide rail units 28, 300, 301, with FIGS. 1 and 2 showing just one guide rail unit 28 in a position arranged on the enclosure 17. The guide rail units 28, 300, 301 are arranged interchangeably on the enclosure 17. In terms of arrangement and/or securing, e.g. interchangeable and/or detachable arrangement and/or interchangeable and/or detachable securing, on the enclosure 17, the different guide rail units 28, 300, 301 are of like construction. The guide rail units 28, 300, 301 in this case differ in the position of the guide rail 31 for guiding the patient table 27 and thus in guide height 39 (see FIG. 5).

To move the patient table 27, the patient positioning apparatus 25 has an adjusting unit 33 and a patient table control unit 34. The adjusting unit 33 has a horizontal adjusting unit 35 and a vertical adjusting unit 36. The horizontal adjusting unit 35 is configured to adjust a position of the patient table 27 in the horizontal direction, e.g. in the z direction and/or in the longitudinal direction 32 of the patient accommodation region 25. The vertical adjusting unit 36 is configured to adjust a height and/or position in the vertical direction 37, e.g. in the y direction of the patient accommodation region 25. The patient table control unit 34 is configured to control the adjusting unit 33 and has the necessary software and hardware for this purpose.

For flexible adjustment of a height and/or vertical position of the patient table 27 within the patient accommodation region 15, the enclosure 17 has at least one securing element 38 for detachable arrangement and/or securing of the guide rail units 28. In the present exemplary embodiment, two guide rail units 28 are arranged within the patient accommodation region 15 on opposing sides of the enclosure 17 (FIG. 2), with the two guide rail units 28 being of like construction in terms of a guide height 39 of the patient table 27. To this end, the enclosure 17 also has at least one securing element on each of the two opposing sides 29, 30 for arranging and/or securing the two guide rail units 28.

In the present exemplary embodiment, the enclosure 17 has two securing elements 38 for arranging and/or securing a guide rail unit 28, e.g. a single guide rail unit 28. The enclosure 17 thus has four securing elements 38 for securing the two guide rail units 28. In one alternative configuration, the enclosure 17 may also have more than two securing elements 38 for arranging and/or securing a guide rail unit 28. The four securing elements 38 are in each case arranged on the enclosure 17 outside the overlap region 40 of the enclosure 17 with the radio-frequency antenna unit 14.

The individual securing elements 38 in each case have a positive-locking element (see FIG. 2). The positive-locking elements are here of like construction. The individual securing elements 38, e.g. positive-locking elements, here in each case comprise a removable peg and/or cylindrical pin, which is secured to the enclosure 17 and protrudes into the patient accommodation region 15. The securing elements 38, e.g. the pegs, are here arranged in such a way on the enclosure 17 that they extend away from the enclosure 17 in the vertical direction 37 and/or in the y direction and protrude into the patient accommodation region 15 (FIG. 2).

To arrange and/or secure the two guide rail units 28 on the enclosure 17, the two guide rail units 28 in each case have two securing elements 41. The securing elements 41 of the two guide rail units 28 are here configured to match the securing elements 38 of the enclosure 17, such that when the securing elements 41 of the guide rail units 28 are connected mechanically to the securing elements 38 of the enclosure 17, reliable arrangement, and/or securing of the guide rail units 28 to the enclosure 17 is achieved. In addition, the number of securing elements 41 of the guide rail units 28 is configured to match the number of securing elements 38 of the enclosure 17. The securing elements 41 of the guide rail units 28 are in this case arranged on a side of the guide rail units 28 facing the enclosure 17. In contrast, the at least one guide rail 31 of the guide rail unit 28 is arranged on a side of the guide rail unit 28 facing the patient accommodation region 15.

The individual securing elements 41 of the guide rail units 28 in this case comprise openings configured to receive the pegs and/or cylindrical pins on the enclosure 17. When securing the guide rail units 28 to the enclosure 17, the pegs and/or cylindrical formation on the enclosure 17 protrude into the openings in the guide rail units 28. The openings may in this case also have a cross-sectionally T-shaped region, in which, for example, mushroom-headed pegs on the enclosure 17 are secured for reliable arrangement and/or securing of the guide rail unit 28.

Figure 3:
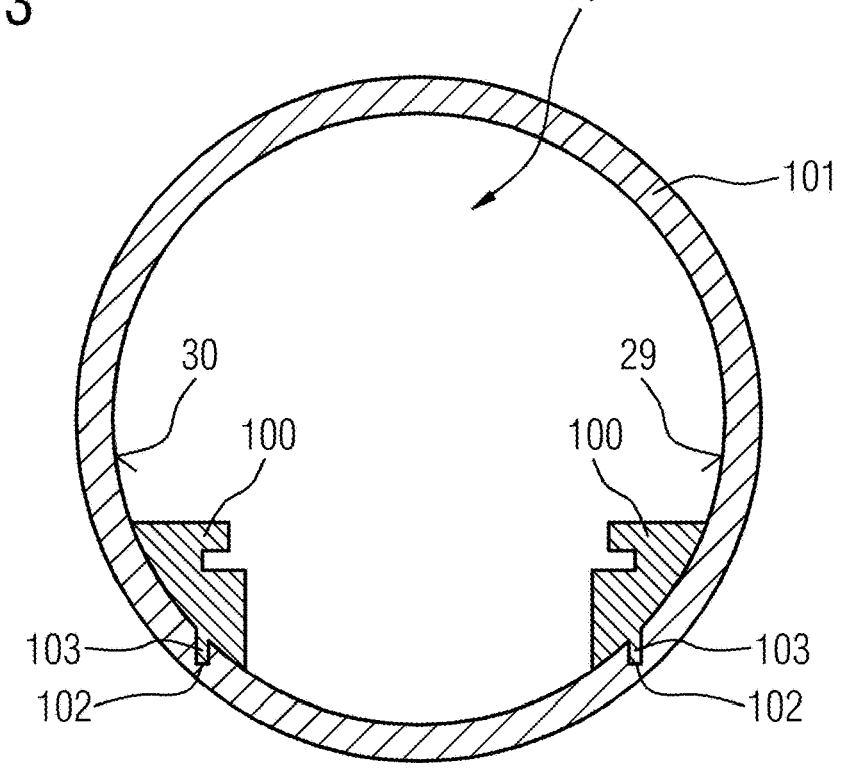
FIG. 3 illustrates an example sectional representation of a detachable arrangement of a guide rail unit on an enclosure, in accordance with one or more embodiments of the disclosure.

FIG. 3 shows an alternative exemplary embodiment of a guide rail unit 100 and an enclosure 101, surrounding the patient accommodation region 15, of a magnetic resonance apparatus 10. Components, features and functions which remain substantially the same are in principle provided with the same reference signs. The following description is limited substantially to the differences relative to the exemplary embodiment in FIGS. 1 and 2, reference being made with regard to components, features and functions that remain the same to the description of the exemplary embodiment in FIGS. 1 and 2.

FIG. 3 shows an enclosure 101, surrounding the patient accommodation region 15, of the magnetic resonance apparatus 10. The enclosure 101 has at least one securing element 102 for detachably arranging and/or securing a guide rail unit 100. In the present exemplary embodiment, the magnetic resonance apparatus 10 has two guide rail units 100 that are arranged on opposing sides 29, 30 of the enclosure 101 surrounding the patient accommodation region 15. The two guide rail units 100 are arranged and/or positioned interchangeably on the enclosure 101.

The enclosure 101 here has two securing elements 102 for detachable and/or interchangeable securing and/or arrangement of each guide rail unit 100. The individual securing elements 102 are in each case formed of positive-locking elements, the positive-locking elements each having a hole and/or opening in the present exemplary embodiment. The securing elements 102, e.g. the openings and/or holes, are in each case arranged on the enclosure 101 outside the overlap region 40 of the enclosure 101 with the radio-frequency antenna unit 14.

In addition, the two guide rail units 100 in each case also have securing elements 103, which are configured to be compatible with the securing elements 102 of the enclosure 101. In the present exemplary embodiment, the securing elements 103 of the guide rail units 100 have pegs and/or pins. For example, the securing elements 103 of the guide rail units 100 may comprise mushroom-headed pegs which engage in the holes and/or openings in the enclosure 101 and thus enable reliable securing, e.g. interlocking, of the guide rail units 100 to the enclosure 101. In addition, the number of securing elements 103 of the guide rail units 100 is configured to match the number of securing elements 102 of the enclosure 101.

Figure 4:
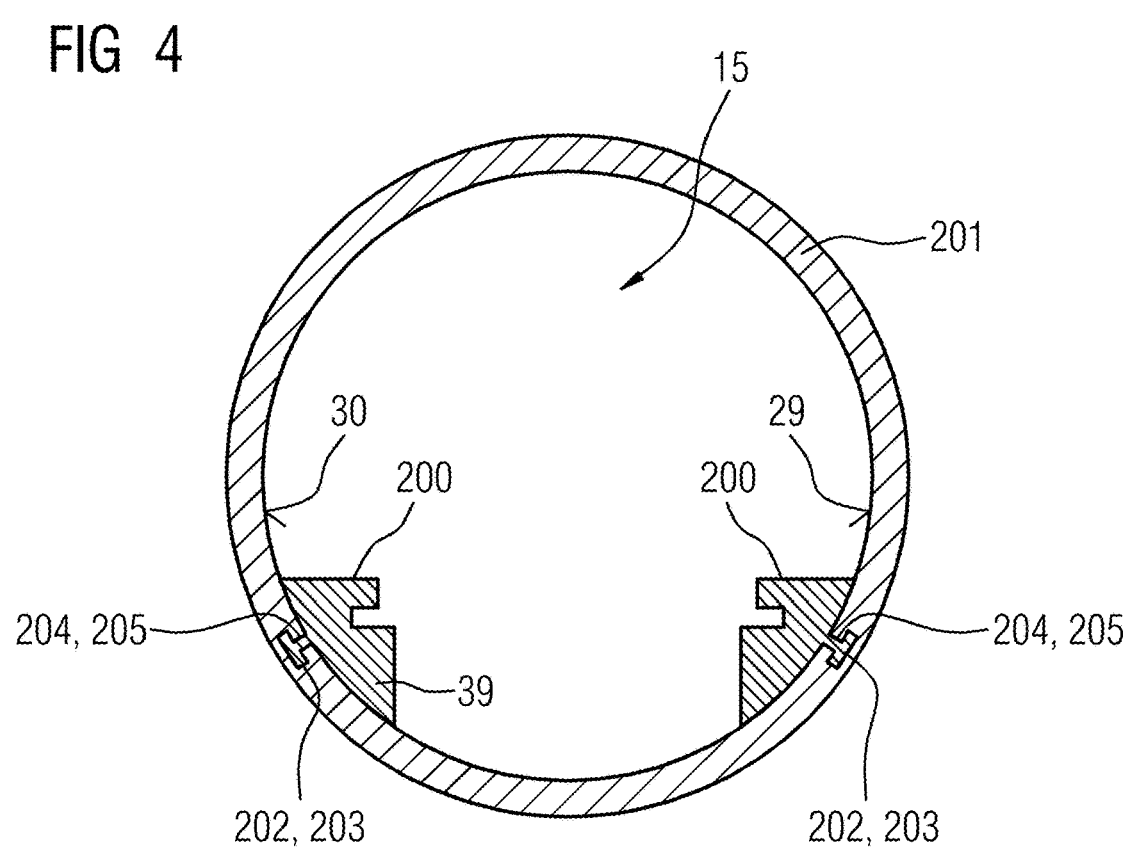
FIG. 4 illustrates a further example sectional representation of a detachable arrangement of a guide rail unit on an enclosure, in accordance with one or more embodiments of the disclosure.

FIG. 4 shows an alternative exemplary embodiment of a guide rail unit 200 and an enclosure 201, surrounding the patient accommodation region 15, of a magnetic resonance apparatus 10. Components, features and functions which remain substantially the same are in principle provided with the same reference signs. The following description is limited substantially to the differences relative to the exemplary embodiments in FIGS. 1 to 3, reference being made with regard to components, features and functions that remain the same to the description of the exemplary embodiment in FIGS. 1 to 3.

FIG. 4 shows an enclosure 201, surrounding the patient accommodation region 15, of the magnetic resonance apparatus 10. The enclosure 201 has one securing element 202 for detachably arranging and/or securing a guide rail unit 200. In the present exemplary embodiment, the magnetic resonance apparatus 10 has two guide rail units 200 that are arranged on opposing sides 29, 30 of the enclosure 201 surrounding the patient accommodation region 15. The two guide rail units 200 are arranged and/or positioned interchangeably on the enclosure 201.

For detachable and/or interchangeable securing and/or arrangement of each guide rail unit 200, the enclosure 201 here has a single securing element 202. The individual securing elements 202 are in each case formed of positive-locking elements and comprise a groove 203 extending in the longitudinal direction 32 of the patient accommodation region 15. The two grooves 203 are configured as a T groove in the present exemplary embodiment. Alternatively, the two grooves 203 may also take the form of a dovetail groove and/or another form which appears appropriate to a person skilled in the art.

As is visible in FIG. 4, the two guide rail units 100 in each case also have a securing element 204 corresponding to the securing elements 202 enclosed by the enclosure 201. In the present exemplary embodiment, the two guide rail units 200 in each case have a T-shaped rail 205 which is insertable into the T-shaped groove in the enclosure 201.

Figure 5:
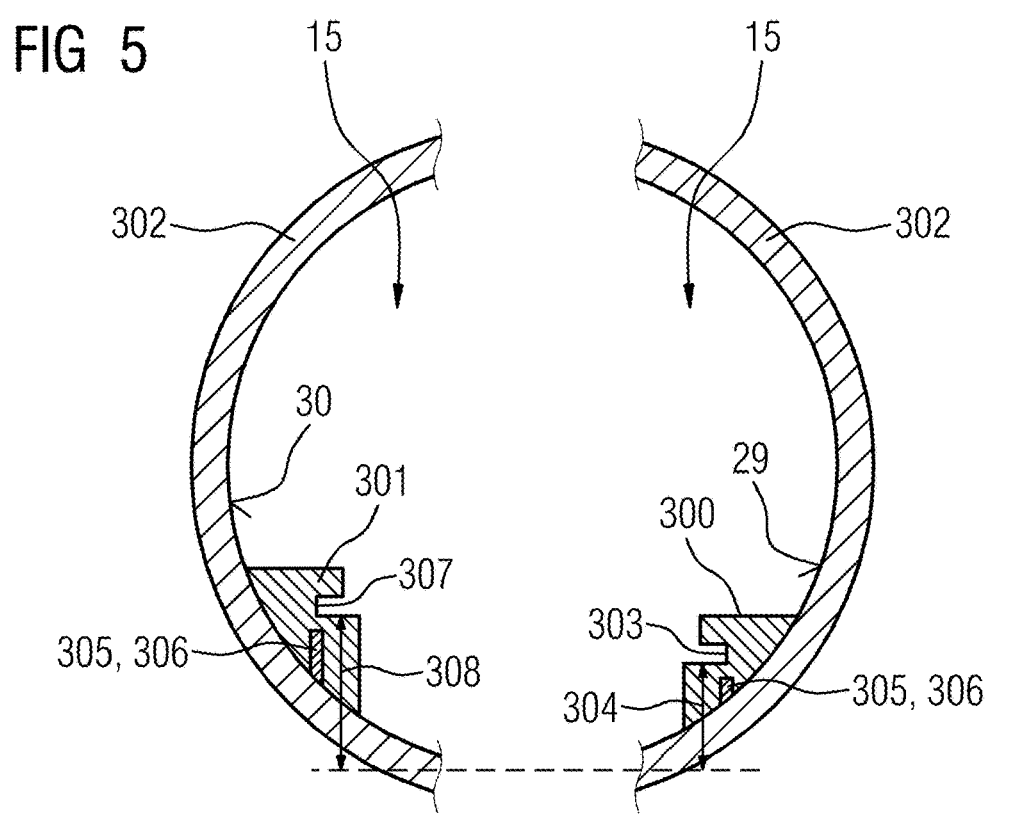
FIG. 5 illustrates an example sectional representation with two different guide rail units on the enclosure, in accordance with one or more embodiments of the disclosure.

FIG. 5 shows an alternative exemplary embodiment of a guide rail unit 300, 301 and an enclosure 302, surrounding the patient accommodation region 15, of a magnetic resonance apparatus 10. Components, features and functions which remain substantially the same are in principle provided with the same reference signs. The following description is limited substantially to the differences relative to the exemplary embodiments in FIGS. 1 to 4, reference being made with regard to components, features and functions that remain the same to the description of the exemplary embodiment in FIGS. 1 to 4.

FIG. 5 shows an enclosure 302, surrounding the patient accommodation region 15, of the magnetic resonance apparatus 10. In the present exemplary embodiment, two different guide rail units 300, 301 are arranged by way of example on the enclosure 302, in order to demonstrate the different positioning options with multiple guide rail units 300, 301. To advance the patient table 27 within the patient accommodation region 15 and/or position the patient table 27 within the patient accommodation region 15, however, two identically constructed guide rail units 300, 301 are needed, which are arranged on opposing sides 29, 30 of the enclosure 302 surrounding the patient accommodation region 15.

The two guide rail units 300, 301 are arranged and/or positioned interchangeably on the enclosure 302. The two different guide rail units 300, 301 are of like construction with regard to securing to and/or arrangement on the enclosure 302, e.g. with regard to detachable securing to and/or arrangement on the enclosure 302. The two different guide rail units 300, 301 are differently configured with regard to arrangement of a guide rail 303, 307 within the patient accommodation region 15. The differently configured guide rail units 300, 301 have different guide heights 304, 308 and/or different vertical positions for guiding the patient table 27.

In the present exemplary embodiment, the two guide rail units 300, 301 in each case have two securing elements 305 configured as openings, which securing elements are configured to receive securing elements 306, configured as securing pins, of the enclosure 302, as described by way of example in FIGS. 1 and 2 for interchangeable arrangement and/or interchangeable securing of the two guide rail units 300, 301 on/to the enclosure 302. In one alternative configuration, the enclosure 302 may also have securing elements 306 configured as openings and/or holes and the guide rail units 300, 301 corresponding securing elements 305 configured as pegs and/or pins, as described by way of example in FIG. 3. In one alternative configuration, the enclosure 302 may also have securing elements 306 configured as grooves and the guide rail units 300, 301 a corresponding securing element 305 configured as a rail, as described by way of example in FIG. 4. Further configurations of the securing elements 305, 306 which appear appropriate to a person skilled in the art are always conceivable.

Figure 6:
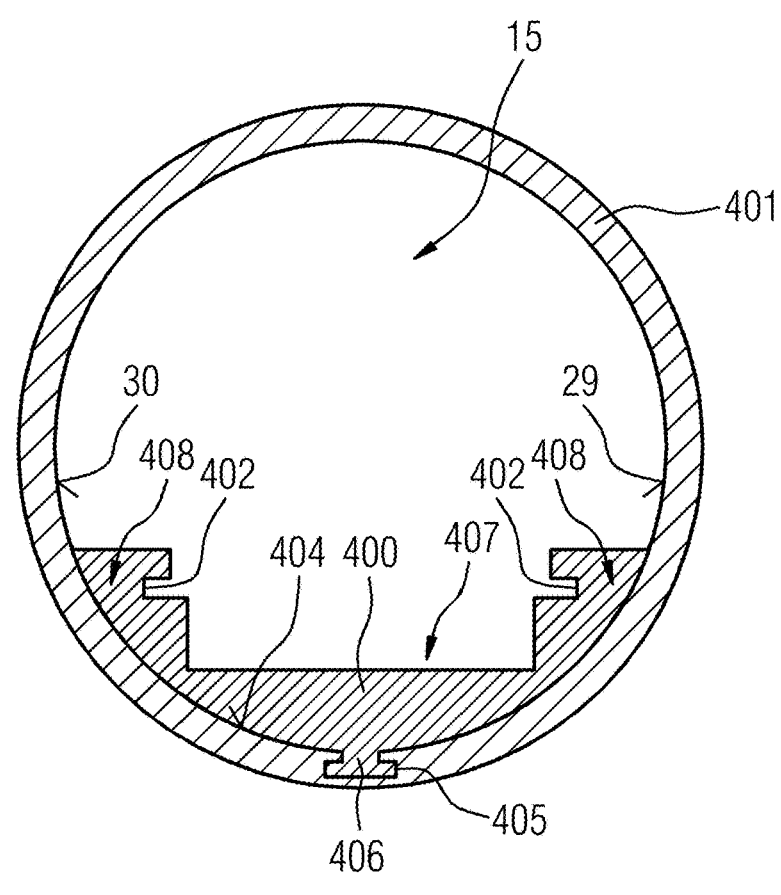
FIG. 6 illustrates a further example of a detachable arrangement of a guide rail unit on an enclosure, in accordance with one or more embodiments of the disclosure.

FIG. 6 shows an alternative exemplary embodiment of a guide rail unit 400 and an enclosure 401, surrounding the patient accommodation region 15, of a magnetic resonance apparatus 10. Components, features and functions which remain substantially the same are in principle provided with the same reference signs. The following description is limited substantially to the differences relative to the exemplary embodiments in FIGS. 1 to 5, reference being made with regard to components, features and functions that remain the same to the description of the exemplary embodiment in FIGS. 1 to 5.

FIG. 6 shows an enclosure 401, surrounding the patient accommodation region 15, of the magnetic resonance apparatus 10. In the present exemplary embodiment, the magnetic resonance apparatus 10 has a single guide rail unit 400 with two guide rails 402. In this case, the guide rail unit 400 is arranged and/or secured interchangeably and/or detachably on/to the enclosure 401.

For detachable and/or interchangeable arrangement of the guide rail unit 400, the enclosure 401 has a securing element 403. The at least one securing element 403 is here arranged on a bottom face 404 of the enclosure 401 surrounding the patient accommodation region 15. The securing element 405 of the enclosure 401 is configured as a groove, by way of example, a corresponding securing element 406 of the guide rail unit 400 taking the form of a rail, as described e.g. in FIG. 4. In one alternative configuration, the securing elements 405, 406 may also be configured as openings and/or holes or as pegs and/or pins, as described in FIGS. 1 and 2 or in FIG. 3.

The guide rail unit 400 additionally has a U-shaped cross-section, the at least one securing element 406 being arranged in a central and/or middle region 407. The guide rails 402 are arranged at side regions 408, which extend upward away from the central region 407. The side regions 408 here in each case rest against opposing sides 29, 30 of the enclosure 401.

Figure 7:
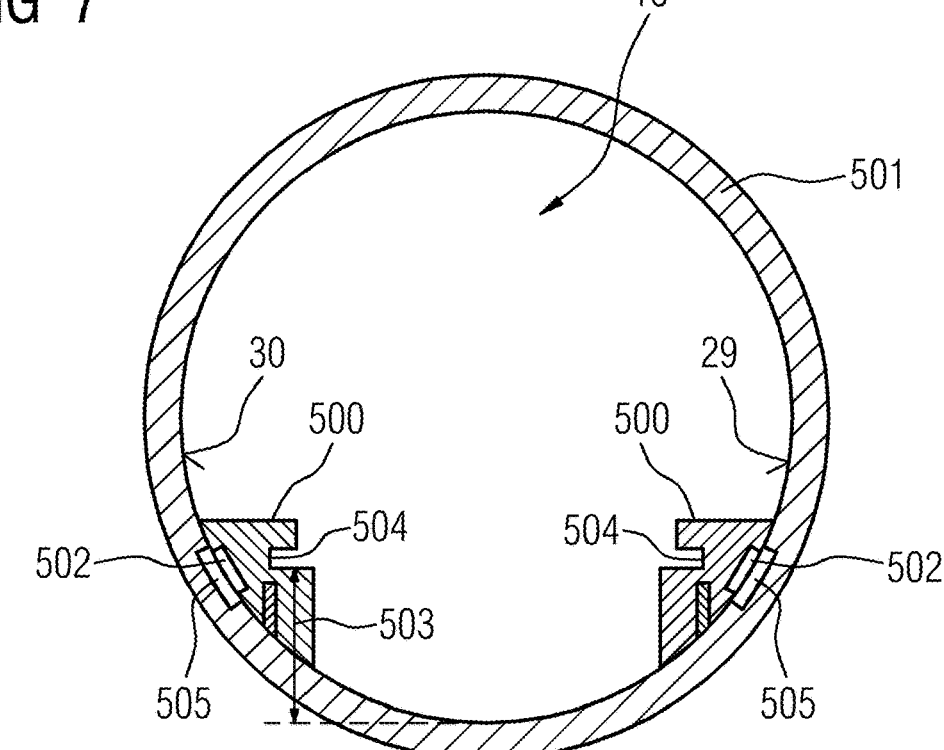
FIG. 7 illustrates a further example of a detachable arrangement of a guide rail unit on the enclosure, the guide rail unit having an encoding, in accordance with one or more embodiments of the disclosure.

FIG. 7 shows an alternative exemplary embodiment of a guide rail unit 500 and an enclosure 501, surrounding the patient accommodation region 15, of a magnetic resonance apparatus 10. Components, features and functions which remain substantially the same are in principle provided with the same reference signs. The following description is limited substantially to the differences relative to the exemplary embodiments in FIGS. 1 to 6, reference being made with regard to components, features and functions that remain the same to the description of the exemplary embodiment in FIGS. 1 to 6.

FIG. 7 shows an enclosure 501, surrounding the patient accommodation region 15, of the magnetic resonance apparatus 10. Two guide rail units 500 are arranged and/or secured interchangeably on/to the enclosure 501 within the patient accommodation region 15. Configuration of the guide rail units 500 and detachable and/or interchangeable securing to and/or arrangement on the enclosure 501 in this case corresponds to the explanations given in relation to FIGS. 1 and 2, to which reference is hereby made. In one alternative configuration, detachable and/or interchangeable securing and/or detachable arrangement of the guide rail units 500 to/on the enclosure 501 may also proceed by way of grooves and rails and/or by way of openings and/or by way of further securing elements which appear appropriate to a person skilled in the art.

The two guide rail units 500 in the present exemplary embodiment in each case have an encoding 502 which enables the at least one guide rail unit 500 to be detected at the position arranged on the enclosure 501. By way of the encoding 502, an item of information relating to a vertical position and/or guide height 503 of a guide rail 504 of the guide rail unit 500 can be determined and/or detected. The magnetic resonance apparatus 10 has at least one detection element 505 for detecting the encoding 502 of the guide rail units 500. In the present exemplary embodiment, the magnetic resonance apparatus 10 has two detection elements 505 that are arranged on the enclosure 501 surrounding the patient accommodation region 15. Alternatively, the detection elements 505 may also be arranged on the patient table 27 of the patient positioning apparatus 25.

In the present exemplary embodiment, the encoding 502 comprises an electro-optical encoding 502, e.g. a barcode. In addition, the detection elements 505 comprise a corresponding sensor element and/or reader element for detecting the electro-optical encoding 502, e.g. the barcode. In one alternative configuration of the encoding 502, the latter may also comprise a mechanical encoding and the detection element 505 a mechanical detection element, such as for example a plug-in connector and/or a pressure switch.

The information detected by the detection elements 505 is transmitted to the patient table control unit 34 via a data transfer unit not depicted in any greater detail. The patient table control unit 34 here comprises a computing module and/or a computing unit (also referred to herein as a controller, computing system, or computer) with a processor which, using the detected encoding 502 and/or using the acquired information of the encoding 502, provides a position of the patient table 27 that is to be established. The position that is to be established here comprises a vertical position and/or height of the patient table 27 into which the latter needs to be brought to allow the patient table 27 to be advanced into the patient accommodation region 15 using the guide rails 504. The position of the patient table 27 that is to be established is here provided by the patient table control unit 34 of the adjusting unit 33, e.g. of the vertical adjusting unit 36.

Figure 8:
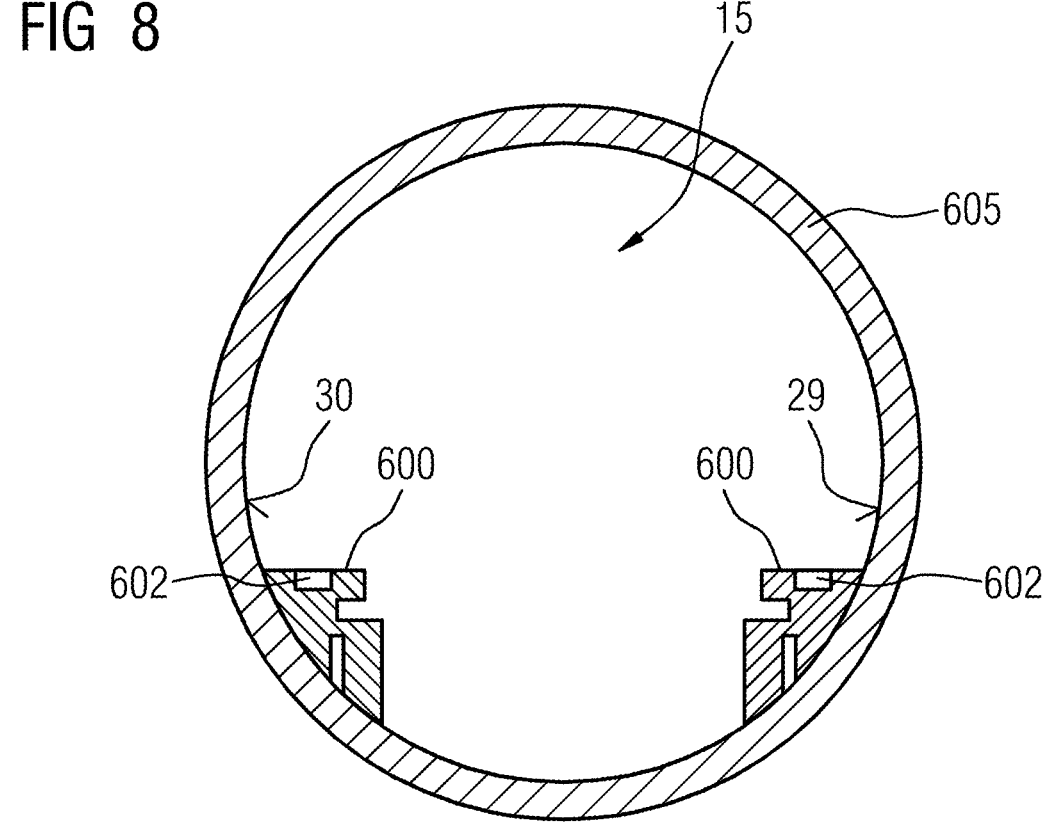
FIG. 8 illustrates a further example of a detachable arrangement of a guide rail unit on the enclosure, the guide rail unit comprising an auxiliary unit, in accordance with one or more embodiments of the disclosure.

FIG. 8 shows an alternative exemplary embodiment of a guide rail unit 600 and an enclosure 601, surrounding the patient accommodation region 15, of a magnetic resonance apparatus 10. Components, features and functions which remain substantially the same are in principle provided with the same reference signs. The following description is limited substantially to the differences relative to the exemplary embodiments in FIGS. 1 to 7, reference being made with regard to components, features and functions that remain the same to the description of the exemplary embodiment in FIGS. 1 to 7.

FIG. 8 shows an enclosure 601, surrounding the patient accommodation region 15, of the magnetic resonance apparatus 10. Two guide rail units 600 are arranged and/or secured interchangeably on/to the enclosure 601 within the patient accommodation region 15. Configuration of the guide rail units 600 and detachable and/or interchangeable securing to and/or arrangement on the enclosure 601 in this case corresponds to the explanations given in relation to FIGS. 1 and 2, to which reference is hereby made. In one alternative configuration, detachable and/or interchangeable securing and/or detachable arrangement of the guide rail units 500 to/on the enclosure 601 may also proceed by way of grooves and rails and/or by way of openings and/or by way of further securing elements which appear appropriate to a person skilled in the art.

The guide rail units 600 in the present exemplary embodiment have an auxiliary unit 602 which is integrated into the guide rail units 600. The auxiliary unit 602 may for example comprise a lighting unit with at least one lighting element and/or light-emitting element for illuminating the patient accommodation region 15. Alternatively or in addition, the auxiliary unit 602 may also comprise a ventilation opening for supplying air to the patient accommodation region 15 during the magnetic resonance examination. Alternatively or in addition, the auxiliary unit 602 may also comprise at least one communication element of a patient communication unit. The magnetic resonance apparatus 10 preferably has a corresponding interface, not depicted in any greater detail, between the guide rail unit 600 and the enclosure 601, so as to enable functionality of the auxiliary unit 602.

Although the disclosure has been illustrated and described in detail with reference to the preferred exemplary embodiment, the disclosure is not restricted by the disclosed examples and other variations may be derived therefrom by the person skilled in the art without going beyond the scope of protection of the disclosure.

Independent of the grammatical term usage, individuals with male, female or other gender identities are included within the term.

The various components described herein may be referred to as "units." Such components may be implemented via any suitable combination of hardware and/or software components as applicable and/or known to achieve their intended respective functionality. This may include mechanical and/ or electrical components, processors, processing circuitry, or other suitable hardware components, in addition to or instead of those discussed herein. Such components may be configured to operate independently, or configured to execute instructions or computer programs that are stored on a suitable computer-readable medium. Regardless of the particular implementation, such units, as applicable and relevant, may alternatively be referred to herein as "circuitry," "controllers," "processors," or "processing circuitry," or alternatively as noted herein.

What is claimed is:

1. A magnetic resonance apparatus, comprising:
a scanner; and
a patient accommodation region at least partially surrounded by the scanner,
wherein the scanner comprises:
an enclosure at least partially surrounding the patient accommodation region; and
a patient positioning apparatus with a movable patient table,
wherein the movable patient table is configured to be advanceable into the patient accommodation region, and
wherein each different guide rail assembly is from among a set of guide rail assemblies and is interchangeably positionable on the enclosure and within the patient accommodation region to provide a different respective guide height for guiding the movable patient table within the patient accommodation region.

2. The magnetic resonance apparatus as claimed in claim 1,
wherein the enclosure comprises at least one securing element for detachable arrangement of one different guide rail assembly from among the set of guide rail assemblies, and
wherein each one of the set of guide rail assemblies comprises at least one securing element corresponding to the at least one securing element of the enclosure.

3. The magnetic resonance apparatus as claimed in claim 2, wherein the at least one securing element of the enclosure comprises a positive-locking element.

4. The magnetic resonance apparatus as claimed in claim 3, wherein the positive-locking element comprises a groove extending in a longitudinal extent of the patient accommodation region.

5. The magnetic resonance apparatus as claimed in claim 1, wherein the enclosure comprises at least two securing elements, which are arranged on the enclosure on opposing sides of the patient accommodation region.

6. The magnetic resonance apparatus as claimed in claim 1, wherein the enclosure comprises at least two securing elements, which are configured to secure each different guide rail assembly from among the set of guide rail assemblies.

7. The magnetic resonance apparatus as claimed in claim 6, wherein the scanner comprises radio-frequency (RF) circuitry, and
wherein each one of the at least two securing elements is arranged on the enclosure outside an overlap region of the enclosure with the RF circuitry.

8. The magnetic resonance apparatus as claimed in claim 6, wherein each one of the at least two securing elements comprises one or more of a hole, an opening, or a peg.

9. The magnetic resonance apparatus as claimed in claim 1, wherein each different guide rail assembly from among the set of guide rail assemblies comprises an encoding for information relating to a respective guide height thereof.

10. The magnetic resonance apparatus as claimed in claim 9, further comprising:
at least one detection element configured to detect the encoding of each different guide rail assembly from among the set of guide rail assemblies.

11. The magnetic resonance apparatus as claimed in claim 10, wherein the at least one detection element is encompassed by the movable patient table of the patient positioning apparatus and/or by the enclosure.

12. The magnetic resonance apparatus as claimed in claim 9, further comprising:
a computing system configured to compute, based upon the encoding, a vertical position of the movable patient table.

13. The magnetic resonance apparatus as claimed in claim 9, wherein the encoding for information relating to a respective guide height of each different guide rail assembly from among the set of guide rail assemblies comprises a mechanical encoding and/or an electro-optical encoding.

14. The magnetic resonance apparatus as claimed in claim 9, wherein the encoding for information relating to a respective guide height of each different guide rail assembly from among the set of guide rail assemblies comprises a barcode.

15. The magnetic resonance apparatus as claimed in claim 9, wherein the encoding for information relating to a respective guide height of each different guide rail assembly from among the set of guide rail assemblies comprises a radio frequency identifier (RFID) code.

16. The magnetic resonance apparatus as claimed in claim 1, further comprising:
at least one auxiliary assembly at least partially integrated into each different guide rail assembly from among the set of guide rail assemblies.

17. The magnetic resonance apparatus as claimed in claim 1, further comprising:
at least one detection element configured to detect an electro-optical encoding disposed on each different guide rail assembly from among the set of guide rail assemblies to determine a respective guide height thereof.

18. The magnetic resonance apparatus as claimed in claim 17, wherein the at least one detection element is encompassed by the movable patient table of the patient positioning apparatus and/or by the enclosure.

* * * * *